(12) United States Patent
Clarke et al.

(10) Patent No.: US 12,226,387 B2
(45) Date of Patent: Feb. 18, 2025

(54) COMPOUNDS FOR USE IN CANCER CACHEXIA

(71) Applicant: TDELTAS LIMITED, Thame (GB)

(72) Inventors: Kieran Clarke, Oxford (GB); Peter Hespel, Thame (GB)

(73) Assignee: TDELTAS LIMITED, Thame (GB)

( * ) Notice: Subject to any disclaimer, the term of this patent is extended or adjusted under 35 U.S.C. 154(b) by 980 days.

(21) Appl. No.: 15/734,159

(22) PCT Filed: Jun. 3, 2019

(86) PCT No.: PCT/GB2019/051532
§ 371 (c)(1),
(2) Date: Dec. 1, 2020

(87) PCT Pub. No.: WO2019/234402
PCT Pub. Date: Dec. 12, 2019

(65) Prior Publication Data
US 2021/0212977 A1 Jul. 15, 2021

(30) Foreign Application Priority Data

Jun. 4, 2018 (GB) .................................... 1809113

(51) Int. Cl.
| | | |
|---|---|---|
| A23L 33/00 | (2016.01) | |
| A23L 33/115 | (2016.01) | |
| A23L 33/125 | (2016.01) | |
| A61K 31/22 | (2006.01) | |
| A61K 47/26 | (2006.01) | |
| A61K 47/44 | (2017.01) | |
| A61P 21/06 | (2006.01) | |

(52) U.S. Cl.
CPC ............ *A61K 31/22* (2013.01); *A23L 33/115* (2016.08); *A23L 33/125* (2016.08); *A23L 33/40* (2016.08); *A61K 47/26* (2013.01); *A61K 47/44* (2013.01); *A61P 21/06* (2018.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 8,642,654 | B2 * | 2/2014 | Clarke .................... | A61P 25/28 |
| | | | | 560/179 |
| 9,801,903 | B2 | 10/2017 | D'Angostino et al. | |
| 10,051,880 | B2 * | 8/2018 | Clarke .................... | A61P 21/00 |
| 10,660,958 | B2 * | 5/2020 | Clarke .................... | A61P 3/10 |
| 11,230,722 | B2 * | 1/2022 | Veech ..................... | C12P 7/62 |
| 11,571,479 | B2 * | 2/2023 | Clarke .................... | A61P 25/00 |
| 2015/0065571 | A1 * | 3/2015 | Clarke .................... | A61K 31/22 |
| | | | | 560/189 |

FOREIGN PATENT DOCUMENTS

| | | |
|---|---|---|
| JP | 2011-192992 | 9/2011 |
| JP | 2013-520454 A | 6/2013 |
| JP | 2016-106274 | 6/2016 |
| WO | 2004/108740 A2 | 12/2004 |
| WO | 2010/021766 A1 | 2/2010 |
| WO | 2013/150153 A1 | 10/2013 |
| WO | 2014/140308 A1 | 9/2014 |
| WO | 2015/018913 A1 | 2/2015 |
| WO | 2018/114309 A1 | 6/2018 |

OTHER PUBLICATIONS

Tisdale et al. "A comparison of long-chain triglycerides and medium-chain triglycerides on weight loss and tumour size in a cachexia model" Br. J. Cancer 1988, 58, 580-583. (Year: 1988).*
Magee et al. The inhibition of malignant cell growth by ketone bodies AJEBAK 1979, 57, 529-539 (Year: 1979).*
Fearon et al. Failure of systemic ketosis to control cachexia and the growth rate of the Walker 256 carcinosarcoma in rats Br. J. Cancer 1985, 52, 87-92 (Year: 1985).*
European Office Action dated Apr. 5, 2023, issued in corresponding European Patent Application No. 19730484.3 (4 pgs.).
M.J. Tisdale et al., "Cancer Cachexia", International Journal of Pancreatology, vol. 7, No. 1-3, 1990 The Human Press Inc., pp. 141-150.
International Preliminary Report on Patentability and Written Opinion of the International Searching Authority issued Dec. 8, 2020 issued in corresponding International Patent Application No. PCT/GB2019/051532 (6 pgs.).
Notice of Reasons for Rejection dated Apr. 18, 2023, issued in corresponding Japanese Patent Application No. 2020-567530 with English translation (7 pgs.).
Notice of Reasons for Refusal dated Feb. 21, 2023, issued in corresponding Japanese Patent Application No. 2022-008547 with English translation (13 pgs.).
Eric C. Woolf et al., "Tumor Metabolism, the Ketogenic Diet and β-Hydroxybutyrate: Novel Approaches to Adjuvant Brain Tumor Therapy", Frontiers in Molecular Neuroscience, vol. 9, Article 122, Nov. 2016, pp. 1-11.
M. J. Tisdale et al., "Cancer Cachexia", International Journal of Pancreatology, vol. 7, 1990, pp. 141-150.
Camila L> P. Oliveira MSc et al., "A Nutritional Perspective of Ketogenic Diet in Cancer: A Narrative Review", J. Acad. Nutr. Diet. 2018, 118, pp. 668-688.
Handbook of Pharmaceutical Excipients, Sixth Edition, Royal Pharmaceutical Society of Great Britain, London, UK, 2009, pp. 1-888.
Bert O. Eijnde PhD et al., "Effect of Muscle Creatine Content Manipulation on Contractile Properties in Mouse Muscles", Muscle Nerve 29, Mar. 2004, pp. 428-435.

(Continued)

*Primary Examiner* — Amanda L. Aguirre
(74) *Attorney, Agent, or Firm* — Finnegan, Henderson, Farabow, Garrett & Dunner, LLP (57) ABSTRACT

The present invention provides a compound for use in treating cancer cachexia in a subject, wherein the compound is of general formula I: (I) or a pharmaceutically acceptable salt or solvate thereof; wherein —$R_1$ is a $C_1$-$C_6$ alkyl group, which alkyl group carries up to five —$OR_2$ substituents, wherein $R_2$ represents hydrogen, or $C_1$-$C_6$ alkyl or wherein —$OR_2$ represents a (R)-3-hydroxybutyrate moiety; or —$R_1$ is a moiety derived from an alcohol HOR1, wherein said alcohol is a sugar. Typically, the invention also provides treatment of the conditions associated with cachexia, such as muscle wasting.

15 Claims, 5 Drawing Sheets

(56) References Cited

OTHER PUBLICATIONS

Wim Derave et al., "Skelatal muscle properties in a transgenic mouse model for amyotrophic lateral sclerosis: effects of creatine treatment", Neurobiology of Disease 13 (2003) pp. 264-272.
Dario Coletti et al., "Substrains of Inbred Mice Differ in Their Physical Activity as a Behavior", The Scientific World Journal, vol. 2013, Article ID 237260, 7 pgs.
Surendra K. Shukla et al., "Metabolic reprogramming induced by ketone bodies diminishes pancreatic cancer cachexia", Cancer & Metabolism 2014, 2:18, 19 pgs.
M.J. Tisdale et al., "A comparison of long-chain triglycerides and medium-chain triglycerides on weight loss and tumour size in a cachexia model", Br. J. Cancer (1988) 58, pp. 580-583.
Search Report dated Dec. 18, 2018 issued in corresponding Great Britain Application No. GB1809113.2 (6 pgs.).
M.J. Tisdale et al., "Reduction of weight loss and tumour size in a chacexia model by a high fat diet", Br. J. Cancer (1987), 56, 39-43.
Kenneth CH Fearon MB, ChB et al., "Cancer cachexia: influence of systemic ketosis on substrate levels and nitrogen metabolism", Am J. Clin. Nutr. 1988; 47; pp. 42-48.
Surendra K. Shukla et al., "Metabolic reprogramming induced by ketone bodies diminishes pancreatic cancer cachexia", Cancer and Metabolism 2014, 2:18, 19 pgs.
Barbara A. Magee et al., "The Inhibition of Malignant Cell Growth by Ketone Bodies", The Australian Journal of Experimental Biology and Medical Science, vol. 57, 1979, pp. 529-539.
International Search Report & Written Opinion of the International Searching Authority dated Aug. 19, 2019 issued in corresponding International Patent Application No. PCT/GB2019/051532 (15 pgs.).
Kieren Clarke et al., "Kinetics, safety and tolerability of (R)-3-hydroxybutyl (R)-3-hydroxybutyrate in healthy adult subjects", Regulatory Toxicology and Pharmacology, 63 (2012) pp. 401-408.
Kieren Clarke et al., "Oral 28-day and developmental Toxicity studies of (R)-3-hydroxybutyl (R)-3-hydroxybutyrate", Regulatory Toxicology and Pharmacology 63 (2012) pp. 196-208.
Erico Chagas Caperuto et al., "β-Hydroxy-β-methylbutyrate supplementation affects Walker 256 tumor-bearing rats in a time-dependent manner", Clinical Nutrition (2007) 26, pp. 117-122.
Kentaro Nakamura et al., "A Ketogenic Formula Prevents Tumor Progression and Cancer Cachexia by Attenuating Systemic Inflammation in Colon 26 Tumor-Bearing Mice", Nutrients 2018, 10, 206, 10 pgs.
First Office Action dated Jan. 18, 2023, issued in corresponding Chinese Patent Application No. 201980038028.5 with English translation (16 pgs.).
Barbara A. Magee et al., "The Inhibition of Malignant Cell Growth by Ketone Bodies", AJEBAK 57 (Pt. 5), pp. 529-539, 1979.
Second Office Action dated Sep. 7, 2023, issued in corresponding Chinese Patent Application No. 201980038028.5 with English translation (15 pgs.).
Examination and Search Report dated Jan. 24, 2022, issued in corresponding Great Britain Patent Application No. GB1809113.2 (8 pgs.).
Kentaro Nakamura et al., "A Ketogenic Formula Prevents Tumor Progression and Cancer Cachexia by Attenuating Systemic Inflammation in Colon 26 Tumor-Bearing Mice", Nutrients, vol. 10, No. 206, 2018, pp. 1-10.
Examination report dated Jun. 7, 2022 issued in corresponding Great Britain Patent Application No. GB1809113.2.
Examination report dated Jun. 7, 2020 issued in corresponding Great Britain Patent Application No. GB1809113.2.
Evans et al., "Effect of Acute Ingestion of β-hydroxybutyrate Salts on the Response to Graded Exercise in Trained Cyclists" *European Journal of Sport Science*, 2018, 18(3), pp. 376-386.
Flint et al., "Tumor-Induced IL-6 Reprograms Host Metabolism to Suppress Anti-Tumor Immunity," *Cell Metabolism*, 2016, vol. 24, pp. 672-684.
Reger et al., "Effects of β-hydroxybutyrate on Cognition in Memory-Impaired Adults" *Neurobiology of Aging*, 2004, 25, pp. 311-314.
Shah and Limketkai, "The Use of Medium-Chain Triglycerides in Gastrointestinal Disorders" *Practical Gastroenterology*, 2017, pp. 20-28.

\* cited by examiner

COMPOUNDS FOR USE IN CANCER CACHEXIA

CROSS-REFERENCE TO RELATED APPLICATIONS

This application is a national stage entry of PCT/GB2019/051532, filed Jun. 3, 2019, which claims priority to Great Britain Patent Application No. 1809113.2, filed Jun. 4, 2018.

FIELD OF THE INVENTION

The present invention relates to compounds for use in preventing or treating cachexia in a subject, specifically the cachexia associated with cancer.

BACKGROUND OF THE INVENTION

Cancer cachexia is a wasting syndrome suffered by cancer patients and characterised by weight loss, anorexia, asthenia and anaemia. It leads to an involuntary loss of muscle in patients. Cachexia adversely affects the patient's ability to fight against infection and withstand chemotherapy and radiotherapy treatment. Consequently, the patient's body begins to waste away.

Reduction in food intake (to <1500 kcal/day), together with a weight loss of 10% or greater and a systemic inflammatory response are considered prognostic parameters of cancer cachexia. The weight loss cannot be reversed with nutritional supplements. Ultimately, cancer cachexia can lead to death, with patients dying when there is 25-30% of total body weight loss.

The mechanism involved in cancer cachexia appears to be complex and multifactorial. The treatment modalities at present include appetite stimulants and drugs against cachexia signalling molecules and mediators, which help prevent and treat wasting.

Ketogenic diets are well known and have been used widely to treat cancer, as discussed in previous U.S. Pat. No. 9,801,903. In general, the ketogenic diet is characterised by high-fat, moderate-to-low protein, and very-low carbohydrate content. The use of a ketogenic diet in cancer has shown potentially promising, but inconsistent results (Oliveira et al; J Acad Nutr Diet, 2017 "A nutritional perspective of ketogenic diet in cancer: A narrative review.") The use of a ketogenic diet is based on the underlying theory of metabolic therapy targeting the abnormal energy metabolism of cancer cells. The ketogenic state restricts glucose availability and impairs glycolysis in cancer cells while providing alternative energy sources for healthy cells. This selectively starves cancer cells, while leaving normal cells unharmed.

Woolf et al in Front Mol Neurosci, November 2016, Vol 9, Article 122 "Tumour metabolism, the ketogenic diet and β-hydroxybutyrate: Novel approaches to adjuvant brain tumour therapy" discloses that the ketogenic diet may be a promising anti-cancer therapy. The paper discusses how the ketogenic diet has been shown to reduce angiogenesis, inflammation, peritumoral oedema, plus tumour migration and invasion. Furthermore, the diet can enhance the efficacy of radiation and chemotherapy in a mouse model of glioma, thus increasing survival. Furthermore, the paper discusses how ketone bodies themselves possess antitumor effects, and therefore ketone supplementation can be effective against some diseases when used alone.

Attempts have been made to reverse cachexia and to selectively deprive a tumour of metabolic substrates for energy production by feeding a ketogenic diet. For example, Tisdale et al in the Br J Cancer (1987) Vol 56, pages 39-43 attempt to reverse cachexia using a diet based on metabolic differences between tumour and host tissues, which aims to selectively feed the host at the expense of the tumour.

GB2517088A discloses the use of ketone body esters to treat muscle breakdown. Cachexia is mentioned in this publication, but cancer cachexia is not specifically disclosed.

There are conflicting references in the literature on whether cancer patients suffering from cachexia should be placed on a ketogenic diet. Tumour cells are known to have a high rate of glucose consumption, to show increased rates of aerobic glycolysis, and to be susceptible to carbohydrate deprivation. Furthermore, many tumours lack certain key mitochondrial enzymes and thus have largely lost the ability to use fat or ketone bodies for energy production. Therefore, the replacement of glucose by ketone bodies is thought to reduce the energy supply to the tumour, while maintaining energy supply to the host. On the other hand, there is some concern that cancer patients might lose too much weight on a ketogenic diet.

It is generally understood that the term "ketone bodies" encompasses three compounds: D-β-hydroxybutyrate, acetoacetate and acetone. D-β-hydroxybutyrate is otherwise known as βHB or (R)-3-hydroxybutyrate. Ketone bodies are produced by the liver from fatty acids during periods of low food intake.

WO2004/108740 discloses nutritional supplements and therapeutic compositions comprising (R)-3-hydroxybutyrate derivatives. The compositions disclosed therein can be used to treat tumours, particularly brain tumours, such as astrocytoma. The treatment of cancer cachexia is not mentioned.

Shukla et al in Cancer Metab (2014) Vol 2 page 18 "Metabolic reprogramming induced by ketone bodies diminishes pancreatic cancer cachexia" disclose the treatment of pancreatic cancer cachexia using the ketone salts, sodium hydroxybutyrate and lithium acetoacetate. Reduced tumour growth and inhibition of muscle and body weight loss are shown. High amounts of ketone salts were used, which would be dangerous if used in vivo.

The administration of ketone salts cannot be used to raise βHB or AcAc concentrations to appropriate levels in humans (for instance, to the range 10 to 20 mM in blood), as such levels of salt could lead to acidosis, high blood pressure and/or kidney failure. It would be impossible for a human to ingest the required amount of salt without vastly exceeding the daily recommended salt dosages. Gastrointestinal distress and hypertension are often the consequence of high salt ingestion.

Accordingly, there is a need for new and effective treatments for treating cancer cachexia in a subject.

SUMMARY OF THE INVENTION

The present invention therefore provides, in a first aspect, a compound for use in preventing or treating cancer cachexia in a subject, wherein the compound is of general formula I:

I or a pharmaceutically acceptable salt or solvate thereof; wherein

R$_1$ is a C$_1$-C$_6$ alkyl group, which alkyl group carries up to five —OR$_2$ substituents, wherein R$_2$ represents hydrogen, or C$_1$—C alkyl or wherein —OR$_2$ represents a (R)-3-hydroxybutyrate moiety; or

R$_1$ is a moiety derived from an alcohol HOR$_1$, wherein said alcohol is a sugar.

The present invention provides, in a second aspect, a compound which is (R)-3-hydroxybutyrate (R)-1,3-butanediol monoester of formula:

for use in the treatment of cancer in a subject.

The present invention provides, in a third aspect, a compound for use in treating cancer in a subject, wherein the compound is of general formula I:

I or a pharmaceutically acceptable salt or solvate thereof; wherein

R$_1$ is a C$_1$—C alkyl group, which alkyl group carries up to five —OR$_2$ substituents, wherein R$_2$ represents hydrogen, or C$_1$—C alkyl or wherein —OR$_2$ represents a (R)-3-hydroxybutyrate moiety; or

R$_1$ is a moiety derived from an alcohol, HOR$_1$, wherein said alcohol is a sugar;

wherein one hour after administration of the compound, blood (R)-3-hydroxybutyrate concentrations in the subject are in the range 1-20 mM.

Further embodiments of the invention include:

A method of treatment of cancer cachexia in a subject comprising administering to the subject a therapeutically effective amount of a compound of general formula I as defined above;

A method of treatment of cancer in a subject comprising administering to the subject a therapeutically effective amount of (R)-3-hydroxybutyrate (R)-1,3-butanediol monoester of formula:

A method of treatment of cancer in a subject comprising administering to the subject a therapeutically effective amount of a compound of general formula I as defined above, wherein one hour after administration of the compound, blood (R)-3-hydroxybutyrate levels in the subject are in the range 1-20 mM;

Use of a compound of general formula I as defined above in the manufacture of a medicament for the treatment of cancer cachexia in a subject;

Use of (R)-3-hydroxybutyrate (R)-1,3-butanediol monoester of formula:

in the manufacture of a medicament for the treatment of cancer in a subject; and Use of a compound of general formula I as defined above in the manufacture of a medicament for the treatment of cancer in a subject, wherein one hour after administration of the compound to the subject, blood (R)-3-hydroxybutyrate levels in the subject are in the range 1-20 mM.

DETAILED DESCRIPTION OF THE INVENTION

The compounds of the invention provide a source of (R)-3-hydroxybutyrate in the body of the subject. As such, the compounds are esters of (R)-3-hydroxybutyrate, which can be broken down by esterases in the body to form (R)-3-hydroxybutyrate.

(R)-3-hydroxybutyrate is a ketone body, as defined in "Metabolic Regulation: A Human Perspective" by K N Frayn.

WO2004/108740 discloses that ketone bodies may be administered directly to subjects to achieve elevated levels of ketone bodies. However, direct administration of ketone salts or acids can be difficult and risky under certain circumstances, and the use of esters has therefore been proposed as a preferred alternative. The manufacture of ketone esters has been disclosed, for instance, in WO2014/140308, which describes processes for producing (R)-3-hydroxybutyl (R)-3-hydroxybutyrate.

An ester of (R)-3-hydroxybutyrate can be produced via a transesterification reaction of ethyl-(R)-3-hydroxybutyrate with an alcohol. This reaction may be enzyme catalysed. For instance, an ethyl ester of (R)-3-hydroxybutyrate and (R)-1,3-butanediol may be reacted together in the presence of immobilized lipase under mild vacuum to remove the resultant ethanol by-product.

In the first embodiment of the invention, the ester of (R)-3 hydroxybutyrate is a compound of general formula I:

wherein
  $R_1$ is a $C_1$-$C_6$ alkyl group, which alkyl group carries up to five —$OR_2$ substituents;
  wherein $R_2$ represents hydrogen, or $C_1$-$C_6$ alkyl or wherein —$OR_2$ represents a (R)-3-hydroxybutyrate moiety; or
  $R_1$ is a moiety derived from an alcohol $HOR_1$, wherein said alcohol is a sugar.

Typically, zero, one or two —$OR_2$ groups represent a (R)-3-hydroxybutyrate moiety. Preferably, only zero or one —$OR_2$ groups represent a (R)-3-hydroxybutyrate moiety.

The $R_1$ moiety is derived from a corresponding alcohol HO—$R_1$. Alcohol HO—$R_1$ may be, for instance, a monoalcohol, a diol, a polyol, or a sugar.

Preferably, in formula I, $R_1$ is a $C_1$-$C_6$ alkyl group substituted with 0,1,2,3,4 or 5 —$OR_2$ substituents. Most preferably, $R_1$ is a $C_1$-$C_6$ alkyl group substituted with 1, 2 or 3 —$OR_2$ substituents, typically 1 or 2 —$OR_2$ substituents.

Preferably, $R_2$ is H.

Preferably, $R_1$ has formula —$CH_2$—CH(OH)—$CH_2$(OH) or —$CH_2$—$CH_2$—CH(OH)—$CH_3$. In these cases, $R_1$ is a moiety derived from an alcohol HO—$R_1$ which corresponds to butanediol and glycerol respectively. The butanediol may be racemic 1,3 butanediol. Most preferably, the alcohol HO—$R_1$ corresponds to R-1,3 butanediol. In this case the group $R_1$ is of formula:

Preferably, the compound used in the first aspect of the invention is a monoester, i.e. in cases where the alcohol HO—$R_1$ comprises more than one pendant hydroxyl, only one of these reacts to form a hydroxybutyrate moiety. Partial esters are compounds wherein the alcohol HO—$R_1$ comprises more than one pendant hydroxyl, and not all of these have reacted to form a hydroxybutyrate moiety.

We have found that (R)-3-hydroxybutyrate (R)-1,3-butanediol monoester and (R)-3-hydroxybutyrate-glycerol partial esters provide high circulating levels of (R)-3-hydroxybutyrate in the blood. Furthermore, these esters provide a surprisingly high level of uptake in the gut, thereby enabling high blood concentrations of (R)-3-hydroxybutyrate to be achieved upon consumption of a drink.

Accordingly, in a preferred embodiment, the invention provides a hydroxybutyrate ester or partial ester, for example (R)-3-hydroxybutyrate (R)-1,3-butanediol monoester and (R)-3-hydroxybutyrate glycerol partial ester for use in treating cancer cachexia in a subject.

Particularly advantageous is (R)-3-hydroxybutyl-(R)-3-hydroxybutyrate as it allows a large rise in blood (R)-3-hydroxybutyrate to be achieved with oral ingestion of a smaller volume of material than with racemic ketones. A subject ingesting this material is more readily able to ingest adequate ketone in order to provide a physiologically beneficial response without risk of physical discomfort (due to, for instance, ingestion of a large volume of liquid, or a bitter/otherwise aversive flavour). The (R)-3-hydroxybutyl-(R)-3-hydroxybutyrate also raises (R)-3-hydroxybutyrate concentrations for a longer period than ketone salts. A lower frequency of doses is then required to maintain higher (R)-3-hydroxybutyrate levels. This also facilitates compliance of the subject with dosing regimens.

Accordingly, a particularly preferred compound for use in the first aspect of the invention is (R)-3-hydroxybutyrate (R)-1,3-butanediol monoester, otherwise known as (R)-3-hydroxybutyl-(R)-3-hydroxybutyrate, of formula:

A further preferred compound of the invention is (R)-3-hydroxybutyrate-glycerol partial ester, i.e. (R)-3-hydroxybutyrate-glycerol monoester or diester.

In a different embodiment of the invention, $R_1$ is derived from an alcohol $HOR_1$, wherein said alcohol is a sugar. The sugar may be selected from altrose, arabinose, dextrose, erythrose, fructose, galactose, glucose, gulose, idose, lactose, lyxose, mannose, ribose, ribulose, sucrose, talose, threose, and xylose.

In cases where $R_1$ is derived from an alcohol $HOR_1$, which is a polyol, the polyol may be selected from glycerol, sorbitol and xylitol.

When the compounds of the invention contain a chiral centre in addition to that depicted in the formulae above, the compounds may be present as racemic mixtures or pure enantiomeric forms.

Compounds of the invention may be present as physiologically compatible salts. For instance, sodium, potassium, calcium or magnesium salts thereof, may be employed.

Administration of the compounds defined above to a subject can treat or prevent cachexia in the subject, especially cachexia in patients suffering from cancer. As detailed above, cachexia is a wasting syndrome suffered by patients characterised by involuntary loss of muscle weight. "Cancer cachexia" is a wasting syndrome experienced by patients suffering from cancer.

In the treatment of the cancer cachexia, the muscle mass of the subject may be maintained or increased. For instance, the compound or composition defined herein may be administered to a subject for a period of time wherein the muscle mass is increased by at least 1 percentage point, preferably by at least 3 percentage points and desirably by at least 5 percentage points. Typically, the compound or composition is administered to the subject at least once a day, for instance 1,2 or 3 times per day. The composition is generally administered to the subject for the duration of, and following, their cancer treatment.

Preferably, the subject's total body weight in maintained or increased during the ingestion of the invention. Generally, in the present invention, the subject's normal intake of food is maintained or increased.

Suitably the compound or composition defined herein, preferably (R)-3-hydroxybutyrate-(R)-1,3-butanediol monoester, is ingested at a level of at least 100 mg per kilogram of body weight of ketone per day. Desirably, the compound is ingested at a level adequate to provide a blood plasma ketone ((R)-3-hydroxybutyrate) concentration of at least 0.1 mM, preferably at least 0.2 mM, more preferably at least 1 mM and optimally at least 2 mM. Generally the blood plasma level of (R)-3-hydroxybutyrate lies within the range 1-20 mM within one hour of administering the compound. Suitably the compound or composition is ingested at a level such that the blood ketone concentration does not exceed 20 mM, suitably does not exceed 10 mM or 8 mM and may not exceed 5 mM.

The blood concentration of ketone will depend on the body weight of the individual and we have found that oral administration of (R)-3-hydroxybutyrate-(R)-1,3-butanediol monoester of at least 300 mg per kilogram of body weight provides a blood plasma concentration of (R)-3-hydroxybutyrate of around 1.5 mM and administration at 500 mg/kg provides at least 3 mM (R)-3-hydroxybutyrate. At a dose of 700 mg/kg of body weight of the subject, the blood (R)-3-hydroxybutyrate concentration is suitably at least 5 mM, preferably 6 mM. Upon oral administration of monoester of 1 g/kg of body weight of the subject, the blood (R)-3-hydroxybutyrate concentration is suitably at least 7 mM, preferably at least 8 mM, especially at least 9 mM. A dosing regime comprises multiple drinks consumed separately.

Blood levels of (R)-3-hydroxybutyrate may be determined by commercially available testing kits, for example, (R)-3-hydroxybutyrate can be measured on whole blood using a handheld monitor and reagent strips (Precision Xtra, Abbott Diabetes Care, UK).

The invention provides treatment or prevention of the conditions associated with cachexia, such as muscle wasting, weight loss and loss of appetite.

In a further embodiment of the invention, administration of the compound or composition defined herein increases the contractile properties of a subject's muscle. This may advantageously lead to improved strength of the subject.

In a further embodiment of the invention, during the treatment of the cachexia, the activity level of the subject may be increased. Accordingly, the subject may feel more desire to engage in physical activity, and become more active during the course of the treatment.

In the treatment of the cachexia, survival of the subject may be enhanced. Accordingly, the subject may live for a longer period of time than without the treatment.

In the treatment of the cachexia, tumour growth may be suppressed.

Muscle mass, contractile properties of a muscle, activity levels of a subject, tumour growth and survival of a subject can be measured in mammals, for instance, mice, by the methods used in the Examples and in humans using bioimpedance, body callipers, activity monitors (e.g. pedometers), dual-energy X-ray (DEXA) scans, CT scans, and MR scans etc.

The term cancer, as used herein, refers to the physiological condition that is typically characterised by unregulated cell growth, i.e. proliferative disorders. Examples of such proliferative disorders include carcinoma, lymphoma, blastoma, sarcoma, and leukemia.

Specifically, administration can treat cachexia associated with colon cancer.

The compound defined herein may administered together with a carbohydrate. The carbohydrate may be, for instance, a simple sugar such as glucose, fructose or maltose. The compound may alternatively (or as well as) be administered together with protein or amino acids.

In a further embodiment of the invention, the compound (R)-3-hydroxybutyrate-(R)-1,3-butanediol monoester, otherwise known as (R)-3-hydroxybutyl (R)-3-hydroxybutyrate, is administered to a subject in a method of treatment of cancer.

The subject may be an animal, preferably a mammal, for instance, a human.

In one embodiment, the compound, for instance (R)-3-hydroxybutyl (R)-3-hydroxybutyrate, is not used to treat cancer of the liver. For instance, the cancer is not a hepatocellular carcinoma. More particularly, the compound may not be used to reduce liver fat in a subject suffering from hepatocellular carcinoma.

The compound of the invention may not be for use in the treatment of a subject suffering from fatty liver disease including non-alcoholic fatty liver disease (NAFLD), non-alcoholic steatohepatitis (NASH), alcoholic steatohepatitis (ASH) and non-alcoholic fatty liver (NAFL), cirrhosis and hepatocellular carcinoma. For instance, the compound may not be for use in reducing liver fat in these subjects.

Preferably, the cancer is colon cancer.

The subject may be suffering from cancer cachexia, as outlined above.

Compounds useful in the invention may be included with nutritional compositions. Suitably the nutritional composition comprises water and a source of (R)-3-hydroxybutyrate. Preferably, the composition comprises an ester of (R)-3-hydroxybutyrate, a flavouring and optionally one or more of a protein, carbohydrate, sugars, fat, fibre, vitamins and minerals. Suitably, the flavouring may comprise a fruit-based flavouring. In one embodiment, the flavouring is suitably bitter, for example coffee, chocolate, and cranberry. A bitter flavouring may be combined with other flavourings such as fruit based flavourings, for example grapefruit, raspberry and cranberry.

Compositions of the invention may comprise mixtures of isomers of the compounds of formula I discussed above.

The composition is suitably organoleptically acceptable. By "organoleptically acceptable" we mean that the composition must possess acceptable sensory properties of taste, colour, feel and odour.

The composition may comprise a mid-chain triglyceride (MCT). If present, the mid-chain triglyceride preferably comprises a mid-chain triglyceride having a formula $CH_2R_a$—$CH_2R_b$—$CH_2R_c$ wherein $R_a$, $R_b$ and $R_c$ are fatty acids having 5 to 12 carbon atoms. Suitably, $R_a$, $R_b$, and $R_c$ are fatty acids containing a six-carbon backbone (tri-C6:0) as tri-C6:0 MCTs are reported to be absorbed rapidly by the gastrointestinal tract.

The composition of the invention may comprise L-carnitine or a derivative of L-carnitine. Examples of derivatives of L-carnitine include decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine. Where a carnitine is employed, suitably the composition of the invention comprises i) a ketone body, preferably a ketone monoester, more preferably a (R)-3-hydroxybutyrate monoester and ii) L-carnitine or a derivative of L-carnitine and optionally an MCT.

Where MCT and L-carnitine or its derivative is employed, suitably the MCT is emulsified with the carnitine. Preferably 10 to 500 g of emulsified MCT is combined with 10 to 2000 mg of carnitine for example 50 g MCT (95% triC8:0) emulsified with 50 g of mono- and di-glycerides combined with 500 mg of L-carnitine. Preferably the level of the source of (R)-3-hydroxybutyrate is greater than the level of the MCT.

Compositions according to the invention may be provided in any suitable form, including a solid, for example a powder, tablet, bar, confectionary product or a granule, a liquid, for example a beverage, a gel, a capsule or any other conventional product form. The composition may be a food product, food supplement, dietary supplement, functional food or a nutraceutical or a component thereof.

Examples of food products into which the composition may be incorporated as an additive include snack bars, cereals, confectionery and probiotic formulations including yoghurts. Examples of beverages include soft beverages, alcoholic beverages, energy beverages, dry drink mixes, nutritional beverages and herbal teas for infusion or herbal blends for decoction in water.

A nutraceutical is a food ingredient, food supplement or food product, which is considered to provide a medical or health benefit, including the prevention and treatment of disease.

In general, a nutraceutical is specifically adapted to confer a health benefit on the consumer. A nutraceutical typically comprises a micronutrient such as a vitamin, mineral, herb or phytochemical at a higher level than would be found in a corresponding regular food product. That level is typically selected to optimise the intended health benefit of the nutraceutical when taken either as a single serving or as part of a diet regimen or course of nutritional therapy.

The compound used in the invention is typically formulated as a nutraceutical.

When in solid form, the composition suitably comprises at least 5% by weight of the compound of the invention, more preferably at least 10% by weight and up to 95% by weight of the composition. Whilst a level of 15 to 30% by weight of a dry composition may be suitable, for example where the composition is a dry powder intended for use with a liquid to produce a liquid composition, a solid bar or product form suitably comprises from 30 to 95%, especially 50 to 95% by weight of the composition.

When the composition is in solid form the composition may further comprise one or more of the following components:
- a diluent for example lactose, dextrose, saccharose, cellulose, corn starch or potato starch;
- a lubricant for example silica, talc, stearic acid, magnesium or calcium stearate and/or polyethylene glycols;
- a binding agent for example starches, arabic gums, gelatin, methylcellulose, carboxymethylcellulose, or polyvinyl pyrrolidone;
- a disintegrating agent such as starch, alginic acid, alginates or sodium starch glycolate;
- an effervescing agent;
- a dyestuff;
- a flavouring;
- a wetting agent, for example lecithin, polysorbates, lauryl sulphates; and/or
- a carrier.

Where the composition is in liquid form, the composition suitably comprises a compound as defined herein at a level of at least 1%, for example 3 to 40% by weight of the liquid composition, but may be higher for example up to 50% by weight of the composition depending on whether the composition is intended to be taken as a single dose or in multiple smaller doses to reach the desired blood ketone level.

The composition in liquid form may comprise several liquid components which are suitably blended together or may comprise liquid and solid components which are mixed with or dissolved in the liquid component as appropriate. In one embodiment, a dry composition comprising the compound define above is diluted with a suitable liquid, for example water, fruit juice, yoghurt or milk, preferably at a ratio of 1:1 to 1:10, more preferably 1:3 to 1:7 of dry composition to liquid.

The composition may be provided, as desired, as a liquid product in a form ready for consumption or as a concentrate or paste suitable for dilution on use. The diluent for use with the liquid composition is preferably milk, fruit juice or water.

If desired, the composition may also be provided in encapsulated form, provided that the encapsulation material and the quantity in which it is used is suitable for safe human consumption.

One aspect of the invention provides compounds of the invention as defined above in a pharmaceutical composition, together with one or more pharmaceutically acceptable excipients.

Compounds used in the invention may be present as pharmaceutically acceptable salts. As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds used in the invention may be present as solvates. The term "solvate" refers to a complex or aggregate formed by one or more molecules of a solute, i.e. compounds of the invention or pharmaceutically-acceptable salts thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The compounds of the invention contain a chiral center. Accordingly, they can be used in the form of a racemic mixture, an enantiomer, or a mixture enriched in one or more stereoisomer. The scope of the invention as described and claimed encompasses the racemic forms of the compounds of the invention as well as the individual enantiomers, and stereoisomer-enriched mixtures.

It will be appreciated that the term "or a pharmaceutically acceptable salt or solvate thereof" is intended to include all permutations of salts and solvates, such as solvates of pharmaceutically-acceptable salts of compounds of the invention.

The pharmaceutical composition comprises a compound of the invention admixed with one or more pharmaceutically acceptable diluents, excipients or carriers. Even though the compounds useful in the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and PJ Weller.

Compositions (both pharmaceutical and nutritional) may comprise an adsorbent that is pharmaceutically acceptable. Suitably the adsorbent adsorbs the compound of the invention in or on the adsorbent. Advantageously, the flavour of the compound (which may be aversive to taste) is experienced to a lesser degree by the user than would be experienced on consumption of the same composition without the adsorbent. Preferably the adsorbent comprises a lattice or voids capable of retaining the compound of the invention. Any adsorbents used or known for use in food products may be employed. Examples of suitable adsorbents include a polymer hydrogel, for example a polymer of a crosslinked polycarboxylate homopolymer or copolymer, a clathrate, a cyclic oligosaccharide, for example cyclodextrins, and milk powder. The adsorbent may be present at any desired level according to the particular formulation and may be from 5% to 80% by weight of the composition, for example from 10 to 50%.

Typically, use of the invention involves administering compounds orally, parenterally or intravenously. Oral administration is preferred.

The present invention also provides a compound, as defined herein, in substantially pure form or in association with one or more pharmaceutically acceptable diluents or carriers for use in treating cancer, specifically cancer cachexia, in a subject.

As used herein, the term "substantially pure form" typically refers to a compound at a purity of 50% or greater, preferably 75% or greater, more preferably 90% or greater, even more preferably 95% or greater, and most preferably 99% or greater.

The following Example illustrates the invention.

EXAMPLE

General Materials and Methods

Animal housing and husbandry—Male Balb/c mice were obtained at 11 weeks of age and housed in polycarbonate cages on a 6:00 am to 6:00 pm light cycle under controlled room temperature (21-23° C.) and humidity (40-60%). Mice were individually housed to allow assessment of individual energy intake and physical activity parameters. Cages contained spruce particles (Lignocel® BK 8/15) bedding, and were changed every three weeks. Enrichment was provided by two cotton pellets, which were replaced during cage changing. Mice received one wooden stick to allow correct wearing off of their teeth while on the liquid diets. Solid food was provided in a recess of the metal wire lid at the top of the cage, whilst liquid diets were provided on a daily basis by means of feeding tubes (Bio-Serv™, catalog #14-726-518). Water was provided by a centralized system with a metal dispenser extending into the cage. All procedures were approved by the Animal Ethics Committee of KU Leuven, Belgium (P093/2017).

Experimental diets—Powdered Lieber-DeCarli diets were purchased from Bio-Serv (products F1258SP and F1259SP; Bio-Serv, Frenchtown, NJ, USA). The control diet (CON) was prepared by adding warm water to the Lieber-DeCarli control diet powder (F1259SP). The ketone-ester diet (KET) was prepared by adding warm water, (R)-3-hydroxybutyl-(R)-3-hydroxybutyrate (ketone ester) and maltodextrin (Canderel, Ternat, Belgium) to the F1258SP powder. A commercially available vanilla flavour (at 0.4% v/v; Dr. Oetker, Diegem, Belgium) was added to both liquid diets to increase palatability. The macronutrient composition of the diets is given in Table 1. Both diets contained equal amounts of energy (kcal), protein, and fat per gram of food.

TABLE 1

Macronutrient composition of the experimental diets.

| Macronutrient (kcal · l$^{-1}$) | Control diet | Ketone-ester diet (4.5%) |
|---|---|---|
| Protein | 151 | 151 |
| Fat | 359 | 359 |
| Carbohydrate | 490 | 275 |
| Ketone | 0 | 215 |
| Total | 1000 | 1000 |

General study protocol and dietary interventions—Mice were individually housed and received ad libitum access to standard chow (Ssniff® R/M-H, Soest, Germany) prior to the start of the study. Food intake was registered and body weight was measured daily for 5 days to assess their normal rate of food intake. Following this baseline follow-up period, the mice were matched for body weight and food intake where after they were randomly assigned to five experimental groups: i) C26 tumour-bearing mice at rest on control diet ($CON_{rest}$), ii) C26-bearing mice at rest on ketone diet ($KET_{rest}$), iii) C26-bearing mice performing voluntary wheel running (WR) on control diet ($CON_{ex}$), iv) C26-bearing mice performing WR on ketone diet ($KET_{ex}$), and v) healthy mice at rest on control diet (WT). Mice were habituated to their experimental diet by a step-wise change of their food supply.

During the first three days, the mice received both their experimental liquid diet (without the addition of ketones) as well as standard chow. From day 3 to 6, mice received only their experimental liquid diets (i.e. 0% KET or CON diet). Thereafter ketone ester was added to the diet in KET groups to yield a 3% concentration on day 6, and a 4.5% concentration on day 9. Matched triplets ($CON_{rest}$, $KET_{rest}$ and WT) and matched pairs ($CON_{ex}$ and $KET_{ex}$) were pair-fed to yield isocaloric diets. CON and WT mice were given food delivering the same energy content (kcal) as their pair-fed KET mice had ingested the day before.

Tumour induction and exercise intervention—On day 12, tumour-xenografts were induced by interscapular injection of 5×10$^5$ murine colon carcinoma C26 cells dissolved in 100 µl of phosphate-buffered saline (PBS). C26 cell line was cultured in DMEM (Thermo Fisher Scientific, 41965-062) supplemented with 10% foetal bovine serum (FBS), 1% glutamine (Sigma G7513) and 1% penicillin and streptomycin. WT mice were injected with an identical volume of PBS. Twenty four hours before tumour inoculation, WR mice ($CON_{ex}$ and $KET_{ex}$) received a running wheel to induce voluntary exercise, as previously reported in Coletti D et al;. Substrains of inbred mice differ in their physical activity as a behavior. Sci World J 2013: 1-7, 2013. Each wheel was supplied with a commercial cycling computer (2Cycle, 81488) to record physical activity parameters (i.e. running time, distance, and speed).

Specific Experimental Methods and Procedures

Survival experiment—Forty mice were randomly assigned to the different experimental groups based on their initial body weight and treated as described above. Mice were allowed to live out their lifespan and were euthanized only when considered moribund. Body weight, food intake and wheel running parameters were measured daily. No additional measurements were performed to avoid confounding effects on survival time.

Behavioural testing and tissue collection experiment—In a second experiment, 9 mice were included in each experimental group and used for behavioural testing and tissue collection. Mice were euthanized 16 days following PBS or tumour cells inoculation. Twenty-four hours before sacrifice the running wheels were removed to eliminate potential acute effects of exercise on variables measured.

Body weight, food intake and wheel running parameters—Body weight was measured every 3 days during the food training period. After tumour induction, body weight was measured at 4-day intervals. Food intake and wheel running parameters were measured daily.

Grip strength—Grip strength of both the forelimbs and the hindlimbs was evaluated, at baseline (day 5) and every 4 days starting at tumour induction, by means of a bar and a grid respectively, connected to an isometric force transducer (BIO-GS3 Grip Strength Test, BIOSEB, Pinellas Park, Florida). Mice were lifted by their tail and positioned to grasp the metal bar or grid, and were pulled horizontally until they could no longer hold the grip. Maximal force (g) was registered during five attempts for both the forelimbs and the hindlimbs. Performance was calculated as the average of the three best attempts. Between attempts the mice were returned to their home cage and given a rest period of 3 min.

Blood metabolite concentrations—Blood parameters were measured 1-hr postprandial, every 3 days during the food habituation period, and every 4 days from the day of tumour induction. Blood βHB and glucose levels were measured using the Glucomen Lx plus-meter (Menarini Diagnostics, Firenze, Italy) with Lx β-ketone or Lx glucose strips, respectively. The detection limits for p-hydroxybutyrate were 0.1 to 8.0 millimolar (mM). Blood lactate concentrations were assessed using the Lactate-Pro 2 monitoring system (Arkray, Kyoto, Japan). Measurements were performed according to the manufacturer's instructions.

Muscle contractile properties—Ex-vivo muscle contractile properties were assessed as described by Derave W et al; Skeletal muscle properties in a transgenic mouse model for amyotrophic lateral sclerosis: Effects of creatine treatment. *Neurobiol Dis* 13: 264-272, 2003 and Eijnde B O et al; Effect of muscle creatine content manipulation on contractile properties in mouse muscles. *Muscle and Nerve* 29: 428-435, 2004.

Mice were anesthetized by an intraperitoneal injection of ketamine-xylazine (10 mg/kg). After dissection of *M. soleus* and *M. extensor* digitorum longus (EDL) of both hindlimbs, muscles were mounted vertically on a force transducer (HSE, March-Hugstetten, Germany) and incubated in organ baths containing Krebs-Henseleit solution (118 mM NaCl, 25 mM NaHCO$_3$, 5 mM KCl, 1 mM MgSO$_4$, 1 mM KH$_2$PO$_4$, 2.5 mM CaCl$_2$ and 1 mM glucose). Organ baths were continuously gassed with a mixture of 95% O$_2$ and 5% CO$_2$ and maintained at 25° C. After mounting, a 15-min stabilization period was allowed to enable recovery from the dissection procedure. Following recovery, resting length (L$_O$) was determined with a micropositioner and an oscilloscope by stimulating the soleus and EDL tetanically for 350 ms at 80 Hz and 120 Hz, respectively, interspersed with 2-min rest intervals. Muscles were subsequently stimulated to evaluate twitch and tetanic characteristics. Muscles were electrically stimulated 3 times at 5 Hz, interspersed with 1-min rest intervals (twitch stimulation), and three times for 500 ms at 80 Hz (Sol) and 250 ms at 100 Hz (EDL) with 2-min rest intervals (tetanic stimulation). Average maximal tension and specific tension (force corrected for muscle cross-sectional area) were calculated for both the twitch and tetanic stimulations. Cross-sectional area was determined by dividing the wet muscle mass by the product of resting muscle length (L$_O$) and the density of mammalian skeletal muscle (1.06 g/cm$^3$).

Statistical analysis—Data are presented as mean±SEM. Differences between experimental groups were evaluated using a two-way analysis of variance (2-way ANOVA), followed by a Tukey's multiple comparisons test to determine which groups differed significantly. Mice from the WT groups were not included in the 2-way ANOVA model, but were added as a reference. Differences in wheel running activity were assessed using an unpaired t-test. For the survival experiment, curves for each experimental group were estimated using the Kaplan-Meier method and differences in survival time were tested using the Log-Rank (Mantel-Cox) test and a Tukey's test to maintain the family-wise Type I error rate at 0.05. Statistical significance was defined as $p<0.05$.

Results

Figure 1:
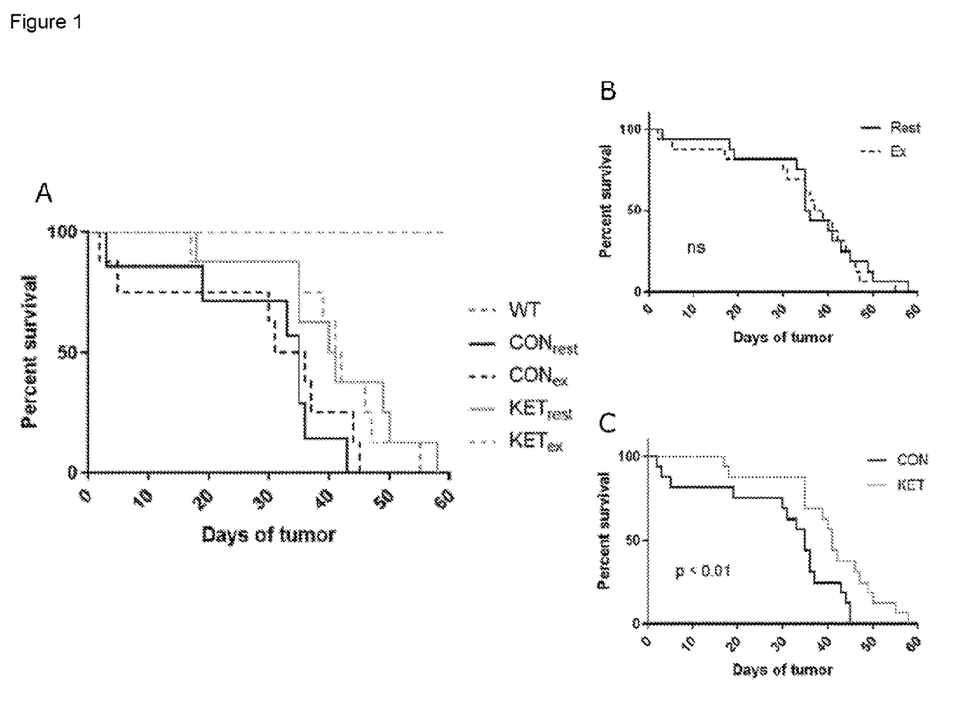
FIG. 1 shows the survival time of mice—(A) Survival curves for all five experimental groups; (B) Main effect of exercise condition; and (C) Main effect of nutritional condition.

FIG. 1 illustrates the survival times—FIG. 1(A) contains survival curves for all five experimental groups; FIG. 1(B) illustrates the main effect of exercise condition (CON$_{rest}$ & KET$_{rest}$ vs. CON$_{ex}$ & KET$_{ex}$); and FIG. 1(C) shows the main effect of nutritional condition (CON$_{rest}$+CON$_{WR}$ vs. KET$_{rest}$+KET$_{ex}$). Mice from the ketone groups showed a substantial increase in both mean and median survival time compared to control groups (+40% and +17%, respectively, $p<0.01$). Survival was similar between the rest and exercise groups.

Figure 2:
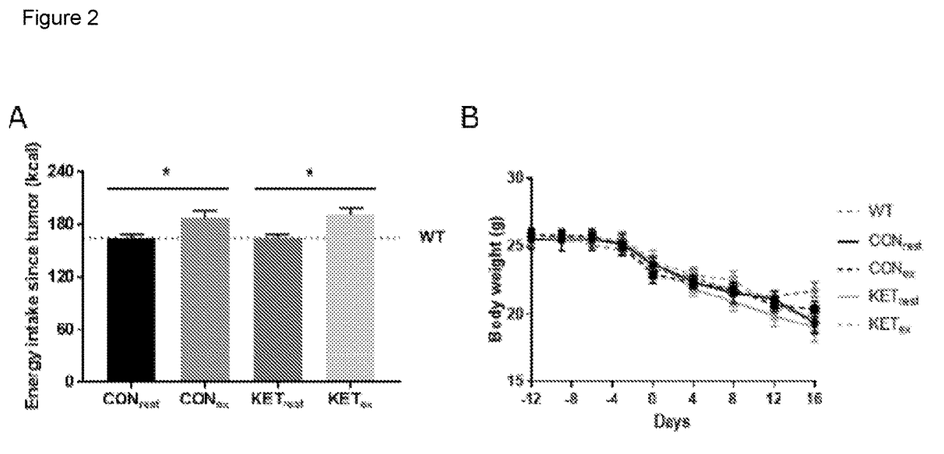
FIG. 2 shows (A) Food intake and (B) body weight for the different experimental groups.

FIG. 2 shows the food intake and body weight—(A) Food intake and (B) body weight for the different experimental groups. Food intake in the exercise groups (CON$_{ex}$ & KET$_{ex}$) was on average ~15% higher than in the rest groups (CON$_{rest}$ & KET$_{rest}$), whilst no differences were observed between KET and CON groups. Body weight similarly decreased over time in all experimental groups.

Figure 3:
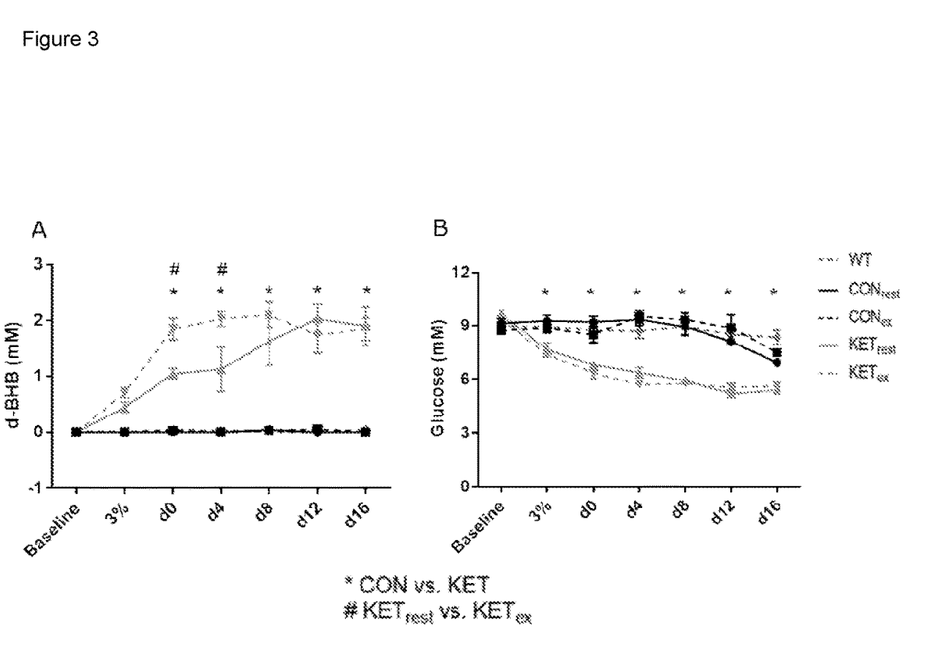
FIG. 3 shows blood parameters—(A) Blood βHB and (B) blood glucose levels for the different experimental groups.

FIG. 3 shows blood parameters—(A) Blood βHB and (B) blood glucose levels for the different experimental groups. At baseline blood βHB levels were undetectable (<0.1 mM) in all groups. During the dietary intervention period, βHB levels increased up to ~2 mM in KET groups, whilst no increase above baseline was found in CON. Compared with CON groups, blood glucose levels were lower in KET at all times.

Figure 4:
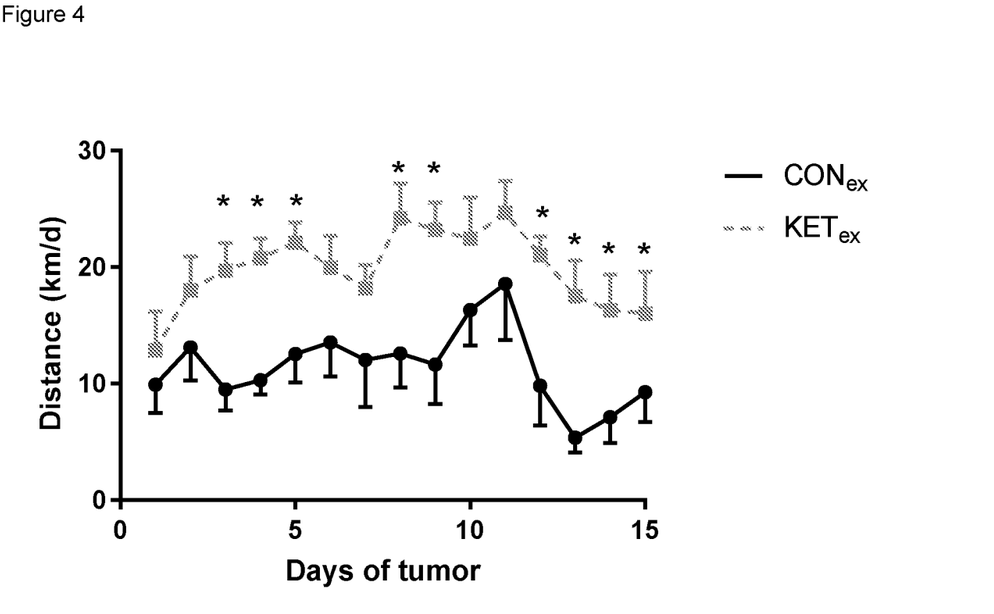
FIG. 4 shows wheel running activity.

FIG. 4 shows wheel running activity. Mice from the KET$_{ex}$ groups showed a substantial increase in wheel running activity compared to CON$_{ex}$, as evidenced by an increase in both running distance (km/day), running speed and duration, as shown in Table 2 below.

TABLE 2

Mouse wheel running activity when consuming either a control or ketone ester diet.

|  | CON$_{ex}$ | KET$_{ex}$ |
| --- | --- | --- |
| Av distance/day (km) | 11.41 ± 1.83 | 19.78 ± 1.36 * |
| Av running speed (km/h) | 2.10 ± 0.23 | 2.94 ± 0.12 * |
| Av running time/day (hh:mm:ss) | 3:15:40 ± 0:25:28 | 6:45:17 ± 0:27:49 * |

Figure 5:
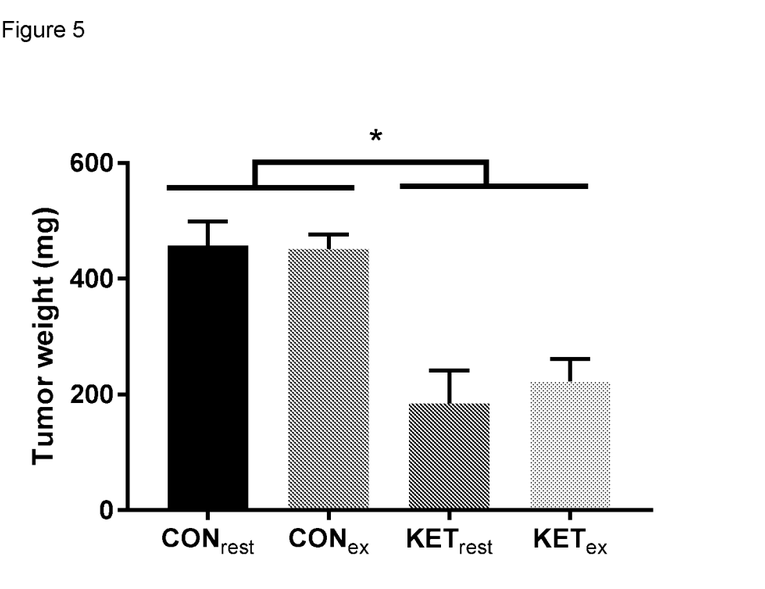
FIG. 5 shows tumour weights.

FIG. 5 shows tumour weights. Compared with CON groups (455±22 mg), KET mice had substantially lower tumour weights (204±32 mg, p<0.05). Tumour weights were similar between the rest and exercise groups.

Figure 6:
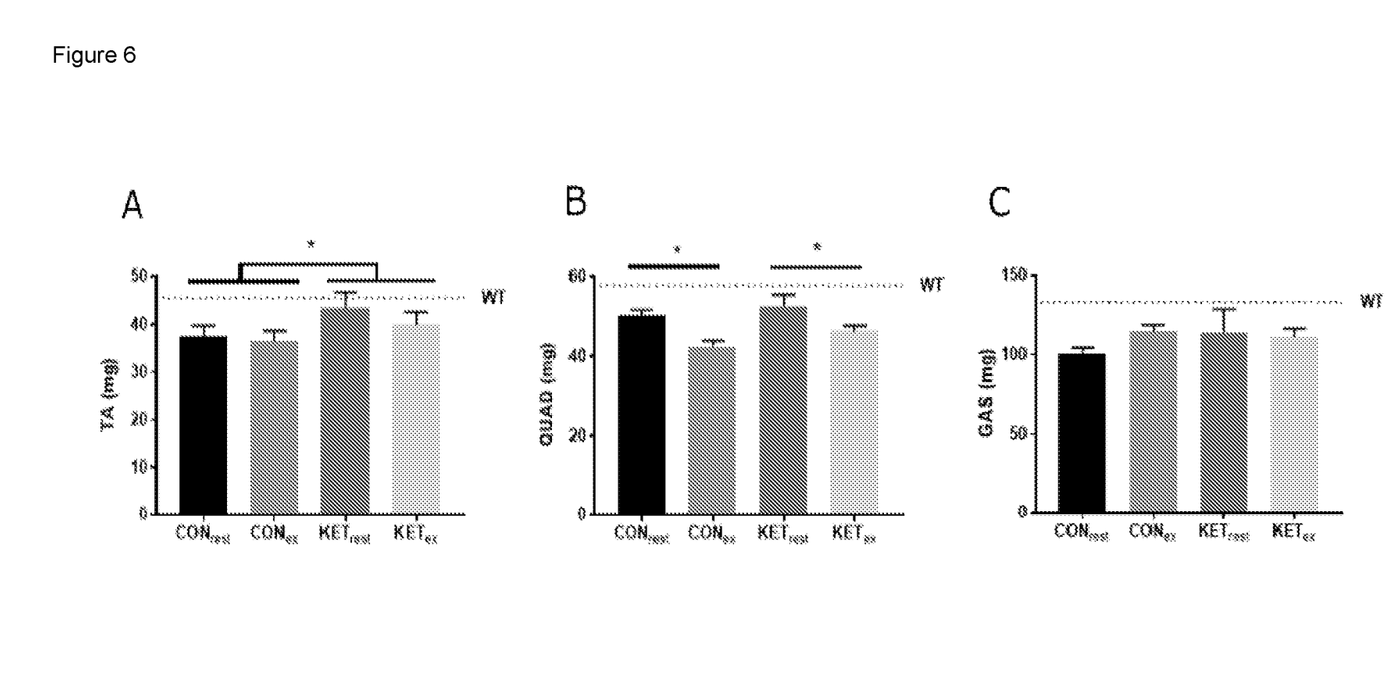
FIG. 6 shows muscle weights—(A) Tibialis anterior (TA), (B) quadriceps (QUAD) and (C) gastrocnemius (GAS) weights for the different experimental groups.

FIG. 6 shows muscle weights—(A) Tibialis anterior (TA), (B) quadriceps (QUAD) and (C) gastrocnemius (GAS) weights for the different experimental groups. Compared with CON (37.0±1.5 mg) TA weight was on average ~12% higher in KET (41.6±2.1 mg, p<0.05). QUAD weights were lower in the exercise groups than in the rest groups (44.4±1.1 vs. 51.4±1.6 mg, p<0.05). GAS weights were similar between the groups.

Figure 7:
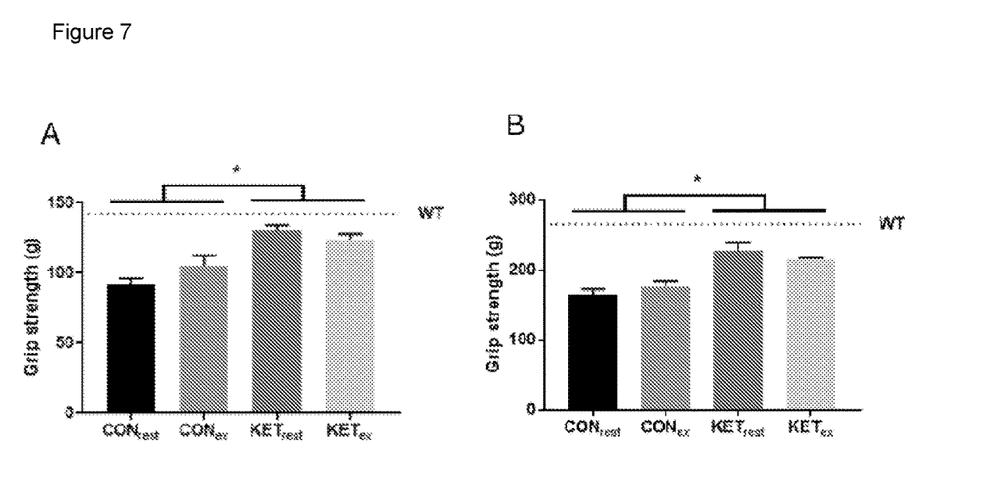
FIG. 7 shows grip strength—(A) Forelimb and (B) hindlimb strength at day 16 for the different experimental groups.

FIG. 7 shows grip strength—(A) Forelimb and (B) hindlimb strength at day 16 for the different experimental groups. Both forelimb and hindlimb grip strength were higher in the ketone groups ($KET_{rest}$ & $KET_{ex}$) than in both the control groups ($CON_{rest}$ & $CON_{ex}$, p<0.05). Exercise per se did not alter grip strength.

Figure 8:
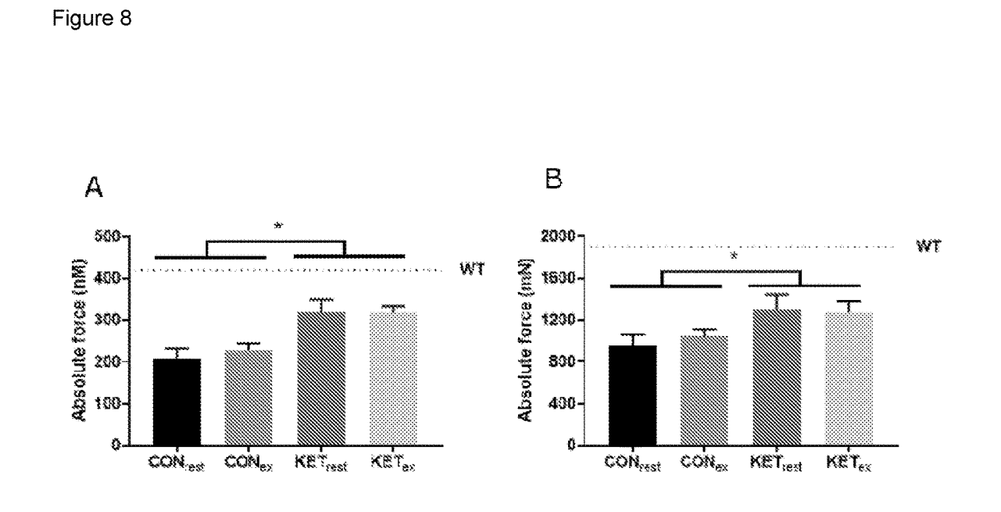
FIG. 8 shows in vitro measured muscle contractile properties of *M. soleus*—peak twitch (A) and tetanus (B) of the *M. soleus* for the different experimental groups.

FIG. 8 shows in vitro measured muscle contractile properties of *M. soleus*—Peak twitch (A) and tetanus (B) of the *M. soleus* for the different experimental groups. Peak twitch and tetanic forces on average were respectively ~45% and ~29% higher in the ketone groups ($KET_{rest}$ & $KET_{ex}$) than in the control groups ($CON_{rest}$ & $CON_{ex}$, p<0.05). Exercise per se did not alter muscle forces.

The invention claimed is:

1. A method of preventing or treating cancer cachexia in a subject, comprising administering to a subject in need thereof a pharmaceutical composition comprising (R)-3-hydroxybutyrate (R)-1,3-butanediol monoester of formula:

wherein
the subject's food intake is not changed.

2. The method of claim 1, wherein the cancer is colon cancer.

3. The method of claim 1, wherein the compound is administered in an amount effective to suppress tumor growth.

4. The method of claim 1, wherein the compound is administered in an amount effective to enhance survival of the subject.

5. The method of claim 1, wherein the compound is administered in an amount effective to maintain or increase muscle mass of the subject.

6. The method of claim 1, further for maintaining or increasing activity levels of the subject.

7. The method of claim 1, wherein the compound is administered together with a carbohydrate compound.

8. The method of claim 1, wherein the pharmaceutical composition further comprises one or more pharmaceutically acceptable excipients.

9. The method of claim 1, wherein the pharmaceutical composition comprises water and one or more of a flavouring, a protein, carbohydrate, sugars fat, fibre, vitamins and minerals.

10. The method of claim 9, wherein the composition further comprises a mid-chain triglyceride, wherein the mid-chain triglyceride has a formula $CH_2R_a$—$CH_2R_b$—$CH_2R_c$, wherein $R_a$, $R_b$, and $R_c$ are fatty acids having 5 to 12 carbon atoms.

11. The method of claim 9, wherein the pharmaceutical composition does not comprise a mid-chain triglyceride.

12. A method of preventing or treating cancer cachexia in a subject without changing the subject's normal intake of food, comprising administering to a subject in need thereof a pharmaceutical composition comprising
(R)-3-hydroxybutyrate (R)-1,3-butanediol monoester of formula:

wherein the pharmaceutical composition is administered in an amount effective to result in a blood plasma concentration of (R)-3-hydroxybutyrate of 0.1 mM to 20 mM after administration.

13. The method of claim 12, wherein the pharmaceutical composition is administered in an amount effective to result in a blood plasma concentration of (R)-3-hydroxybutyrate of 1 mM to 20 mM within one hour of administration.

14. The method of claim 1, wherein the pharmaceutical composition is administered to the subject at least 2 or 3 times per day.

15. The method of claim 12, wherein the pharmaceutical composition is administered in an amount effective to result in a blood plasma concentration of (R)-3-hydroxybutyrate of at least 2 mM.

* * * * *

UNITED STATES PATENT AND TRADEMARK OFFICE
CERTIFICATE OF CORRECTION

PATENT NO. : 12,226,387 B2
APPLICATION NO. : 15/734159
DATED : February 18, 2025
INVENTOR(S) : Kieran Clarke and Peter Hespel Page 1 of 1

It is certified that error appears in the above-identified patent and that said Letters Patent is hereby corrected as shown below:

On the Title Page

Item (57) Abstract, Line 8, "HORI" should read as —$HOR_1$—.

Signed and Sealed this
Fifteenth Day of April, 2025

Coke Morgan Stewart
*Acting Director of the United States Patent and Trademark Office*